United States Patent [19]

Engels et al.

[11] Patent Number: 4,832,959

[45] Date of Patent: May 23, 1989

[54] PREPARATION OF POLYPEPTIDES HAVING HUMAN γ-INTERFERON ACTIVITY

[75] Inventors: Joachim Engels, Kronberg/Taunus; Michael Leineweber, Frankfurt am Main, both of Fed. Rep. of Germany; Eugen Uhlmann, Belmont, Mass.; Wolfgang Ulmer, Frankfurt am Main, Fed. Rep. of Germany

[73] Assignee: Hoechst Aktiengesellschaft, Frankfurt am Main, Fed. Rep. of Germany

[21] Appl. No.: 707,554

[22] Filed: Mar. 4, 1985

[30] Foreign Application Priority Data

Apr. 19, 1984 [DE] Fed. Rep. of Germany ....... 3414831

[51] Int. Cl.⁴ .................. A61K 45/02; C07K 13/00; C12P 21/00
[52] U.S. Cl. .................. 424/85.5; 530/351; 435/68; 435/811
[58] Field of Search .................. 424/85, 85.5; 435/172.3, 68; 530/351

[56] References Cited

U.S. PATENT DOCUMENTS 4,457,867  7/1984  Ishida .................. 530/351
4,604,284  8/1986  Kung et al. .................. 530/351

FOREIGN PATENT DOCUMENTS 0089676  3/1983  European Pat. Off. .
0095350  5/1983  European Pat. Off. .
83/04053 11/1983  PCT Int'l Appl. .

OTHER PUBLICATIONS

Devos et al., Nuclear Acid Research, vol. 10, pp. 2487–2501, 1982.
Gray et al., Nature, vol. 295, pp. 503–508, 1982.
Shepard et al., Nature, vol. 294, pp. 563–565, 1981.
Search Report issued in corresponding European Patent Application, EP 85 104 501.3.

*Primary Examiner*—Blondel Hazel
*Attorney, Agent, or Firm*—Finnegan, Henderson, Farabow, Garrett & Dunner

[57] ABSTRACT

Partial sequences of human-γ-interferon, comprising aminoacid sequences 5 to 127, 1 to 127 and 5 to 146, having biological activity. These partial sequences can be obtained by a genetic engineering process, for which purpose the appropriate DNA sequences are chemically synthesized. The DNA sequences are incorporated in hybrid plasmids, and the latter are introduced into host organisms and their expression is induced there. The biologically active polypeptides are suitable, as is human-γ-interferon, for medicaments.

2 Claims, 2 Drawing Sheets

PREPARATION OF POLYPEPTIDES HAVING HUMAN γ-INTERFERON ACTIVITY

The invention relates to a process for the preparation of polypeptides which exhibit the biological and immunological activity of human gamma interferon, to chemically synthesized genes which code for these peptides, and to suitable vector constructions and host organisms for the expression of these polypeptides. The invention also relates to new polypeptides from which have been deleted, in contradistinction to gamma interferon, partial sequences which are inessential for biological activity. Compared with gamma interferon, these new polypeptides have increased stability or solubility and vary in the specificity of their antiviral activity, but they all resemble gamma interferon in being utilizable as antiviral, antitumoral, antineoplastic or immunomodulating products.

Gamma interferon (previously called immune interferon or type II interferon; abbreviated in this text to IFN-γ) was discovered in 1965 by F. Wheelock (Wheelock; Science 149 (1965), 310) who showed that IFN-γ is able to protect certain cells from virus infection. Human IFN-γ (for basic information, see W. E. Stewart, II, The Interferon System, published by Springer (2nd ed., 1981)) is a polypeptide composed of 146 aminoacids (Gray et al., Nature 295 (1982), 503) which is naturally glycosylated. The glycoprotein has a molecular weight of about 63,000–73,000 (Pestka et al., J. Biol. Chem. 258 (1983), 9706) and its functional form is probably a tetramer. Glycosylation of IFN-γ is not necessary for its functioning; thus, glycosidase treatment of IFN-γ does not reduce its antiviral activity in cell cultures of human fibroblasts (Kelker et al., J. Biol. Chem. 258 (1983), 8010).

Furthermore, in contrast to alpha interferons and beta interferon, IFN-γ is unstable at pH 2 and is also deactivated by heat (60° C.).

The isolation of human IFN-γ from cell cultures of human cell lines or from leukocytes (banked blood) is possible only with poor yields and with low purity of the product. The invention relates to the preparation by genetic engineering methods of polypeptides having properties resembling gamma interferon. Human IFN-γ has the following peptide sequence (Devos et al., Nucl. Acids Research 10 (1982), 2487):

$Cys^1$—Tyr—Cys—Gln—Asp—Pro—Tyr—Val—Lys—$Glu^{10}$—

Ala—Glu—Asn—Leu—Lys—Lys—Tyr—Phe—Asn—$Ala^{20}$—

Gly—His—Ser—Asp—Val—Ala—Asp—Asn—Gly—$Thr^{30}$—

Leu—Phe—Leu—Gly—Ile—Leu—Lys—Asn—Trp—$Lys^{40}$—

Glu—Glu—Ser—Asp—Arg—Lys—Ile—Met—Gln—$Ser^{50}$—

Gln—Ile—Val—Ser—Phe—Tyr—Phe—Lys—Leu—$Phe^{60}$—

Lys—Asn—Phe—Lys—Asp—Asp—Gln—Ser—Ile—$Gln^{70}$—

Lys—Ser—Val—Glu—Thr—Ile—Lys—Glu—Asp—$Met^{80}$—

Asn—Val—Lys—Phe—Phe—Asn—Ser—Asn—Lys—$Lys^{90}$—

Lys—Arg—Asp—Asp—Phe—Glu—Lys—Leu—Thr—$Asn^{100}$—

Tyr—Ser—Val—Thr—Asp—Leu—Asn—Val—Gln—$Arg^{110}$—

Lys—Ala—Ile—His—Glu—Leu—Ile—Gln—Val—$Met^{120}$—

-continued

Ala—Glu—Leu—Ser—Pro—Ala—Ala—Lys—Thr—$Gly^{130}$—

Lys—Arg—Lys—Arg—Ser—Gln—Met—Leu—Phe—$Arg^{140}$—

Gly—Arg—Arg—Ala—Ser—$Gln^{146}$.

One aspect of the present invention relates to the preparation of biologically active partial sequences of human IFN-γ, in particular the partial sequences 1–127, 5–146 and 5–127 of the above sequence.

It is known that the genetic code is "degenerate", that is to say only two aminoacids are coded for by a single nucleotide sequence, while the remaining 18 genetically codable aminoacids may be assigned to 2 to 6 triplets. Moreover, the host cells of different species do not always make the same use of the possible variations arising from this. Thus, there is a vast variety of codon possibilities for the synthesis of the genes. It has now been found that the DNA sequence I (attachment), which codes for the entire aminoacid sequence 1–146, and the DNA sequences IA, IB and IC, which are derived from the latter, are particularly advantageous for the synthesis by genetic engineering methods of polypeptides having IFN-γ activity. The codon for methionine ("triplet No. 0") and, upstream, a "protruding" DNA sequence corresponding, for example, to the restriction endonuclease Eco RI, follow at the 5' end of the coding strand of DNA sequence I, while one stop codon or, preferably, two stop codons and—immediately thereafter or separated by a DNA sequence—a sequence characteristic for a restriction enzyme, for example the single-stranded protruding sequence corresponding to restriction enzyme Sal I, follow at the 3' end of the coding strand. Different recognition sequences ensure the insertion of the DNA into plasmids in the desired orientation.

The codon for the aminoacid methionine at the 5' end of the coding strand can be replaced by a presequence (also called a signal or leader sequence) of a bacterial protein or other protein intrinsic to the host (review article: Perlman and Halvorson; J. Mol. Biol. 167 (1983), 391) which brings about the secretion of the desired polypeptide from the cytoplasm and which, during this excretion process, is eliminated by a signal peptidase which occurs naturally in the host cell.

Two internal unique restriction sites for the restriction enzymes Bam HI and Hind III (in codons 34 and 97 respectively of the coding strand or in codons 35 and 98 respectively of the non-coding strand) make it possible to subclone three gene fragments IFN-I, IFN-II and IFN-III (see DNA sequence II) which can be incorporated in cloning vectors which have been thoroughly investigated, such as, for example, pBR 322 or pUC 8. In addition, a number of other unique recognition sequences for restriction enzymes are incorporated within the structural gene, and these provide, on the one hand, access for partial sequences of IFN-γ and, on the other hand, permit the introduction of variations:

| Restriction enzyme | Cut after nucleotide No. (coding strand) |
|---|---|
| Ava II[a] | 20 |
| Alu I[b] | 39 |
| Hinf I[a] | 134 |
| Dde I[c] | 159 |
| Aha III[c] | 199 |
| Taq I[c] | 294 |
| Aha III[d] | 327 |
| Sst I[a] | 357 |

| Restriction enzyme | Cut after nucleotide No. (coding strand) |
|---|---|
| Bst NI[d] | 362 |
| Pst I[a] | 388 |
| Bbv I[a] | 398 |
| Sst II[a] | 430 |
| Dde I[d] | 444 |

[a]unique with respect to the total DNA sequence I
[b]unique with respect to partial sequence IFN-I
[c]unique with respect to partial sequence IFN-II
[d]unique with respect to partial sequence IFN-III DNA sequence I together with the sequences at its ends can be constructed of 34 oligonucleotides having lengths of from 18 to 33 nucleotides (see DNA sequence II) by first chemically synthesizing the latter and then linking them enzymatically via "sticky ends" of from 4 to 6 nucleotides.

Furthermore, in DNA sequence I, attention has been paid to those aminoacids to which several codons may be assigned so that the latter are not equivalent but, on the contrary, exhibit different preferences in the particular host cell, such as E. coli. Furthermore, palindromic sequences have been reduced to a minimum.

Thus, the gene structure of DNA sequence I can easily be produced from relatively small structural units, it permits the subcloning of three gene fragments in wellknown vectors, and it permits the fragments to be combined to give the total gene and permits the latter to be modified. Thus, after cloning the gene with DNA sequence I, DNA partial sequences can be obtained from the latter by cleavage with certain restriction enzymes, in particular the partial sequences IA, IB and IC, which code for the interferon partial sequences corresponding to aminoacids 1–127, 5–146 and 5–127.

An example of a partial sequence is provided by DNA sequence IA, which leads to a polypeptide having the first 127 aminoacids of IFN-γ, DNA sequence I being modified in such a manner that one stop triplet or, preferably, two stop triplets and the sequence characteristic for a restriction enzyme, for example the protruding end for restriction enzyme Sal I, are directly connected to triplet No. 127.

On the other hand, cutting DNA sequence I with restriction endonuclease Ava II and ligation of an adaptor sequence with the large fragment thus obtained results in a DNA sequence IB in which the codons for the first four aminoacids of IFN-γ have been deleted, that is to say methionine is located immediately upstream of aminoacid No. 5 (aspartic acid). A DNA sequence IC, which codes for a polypeptide having aminoacids 5–127 of IFN-γ, can be generated from this DNA sequence IB via the Pst I restriction site.

The incorporation of the synthetic genes or gene fragments into cloning vectors, for example into the commercially available plasmids pUC 8 and pBR 322 or in other generally available plasmids, such as ptac 11 and pKK 177.3, is carried out in a manner known per se. It is also possible previously to provide the chemically synthesized genes with suitable chemically synthesized control regions which permit expression of the proteins. In this context, reference may be made to the textbook by Maniatis (Molecular Cloning, Maniatis et al., Cold Spring Harbor, 1982). The transformation of the hybrid plasmids thus obtained into suitable host organisms, advantageously into E. coli, is likewise known per se and is described in detail in the textbook mentioned above. THe isolation of the expressed protein and its purification are likewise described (J. A. Georgiades, Texas Reports in Biology and Medicine 41 (1981) 179; Came and Carter (editors), "Interferons and Their Applications", published by Springer 1984).

The polypeptides which are obtained according to the invention and have gamma interferon activity in accordance with DNA sequences IA, IB and IC are new and the invention relates to them. The same applies to DNA sequences modified from the new DNA sequence I, gamma interferon analogs obtainable from these sequences, the gene fragments IFN-I, IFN-II and IFN-III and their modifications, the hybrid plasmids obtained with them, and the transformed host organisms.

Further embodiments of the invention are set out in the patent claims.

Some other embodiments of the invention are illustrated in detail in the examples which follow, from which the multiplicity of possible modifications and combinations are evident to those skilled in the art. In these examples, percentage data relate to weight unless otherwise specified.

EXAMPLES

1. Chemical Synthesis of a Single-Stranded Oligonucleotide

The synthesis of the structural units of the gene is illustrated using the example of structural unit Ia of the gene, which comprises nucleotides 1–23 of the coding strand. Using known methods (M. J. Gait et al., Nucleic Acids Res. 8 (1980) 1081–1096)), the nucleoside located at the 3' end, thus, in the present case, cytidine (nucleotide no. 23), is covalently bonded via the 3'-hydroxyl group to silica gel (®FRACTOSIL, supplied by Merck). For this purpose, the silica gel is first reacted with 3-(triethoxysilyl)propylamine with elimination of ethanol, a Si-O-Si bond being produced. The cytidine is reacted in the form of the $N^4$-benzoyl-3'-0-succinoyl-5'-dimethoxytrityl ether with the modified carrier in the presence of paranitrophenol and N,N'-dicyclohexylcarbodiimide, the free carboxyl group of the succinoyl group acylating the amino radical of the propylamino group.

In the steps of the syntheses which follow, the base component is used as the dialkylamide or chloride of the monomethyl ester of the 5'-0-dimethoxytritylnucleoside-3'-phosphorous acid, the adenine being in the form of the $N^6$-benzoyl compound, the cytosine in the form of the $N^4$-benzoyl compound, the guanine in the form of the $N^2$-isobutyryl compound, and the thymine, which contains no amino group being without a protective group.

50 mg of the polymeric carrier which contains 2 μmol of bound cytosine are treated consecutively with the following agents:
(a) nitromethane,
(b) a saturated solution of zinc bromide in nitromethane containing 1 % water,
(c) methanol,
(d) tetrahydrofuran,
(e) acetonitrile,
(f) 40 μmol of the appropriate nucleoside phosphite and 200 μmol of tetrazole in 0.5 ml of anhydrous acetonitrile (5 minutes),
(g) 20 % acetic anhydride in tetrahydrofuran containing 40 % lutidine and 10 % dimethylaminopyridine (2 minutes),
(h) tetrahydrofuran, (i) tetrahydrofuran containing 20 % water and 40 % lutidine,
(j) 3 % iodine in collidine/water/tetrahydrofuran in the ratio by volume 5:4:1,
(k) tetrahydrofuran and
(l) methanol.

The term "phosphite" in this context is to be understood to be the monomethyl ester of the deoxyribose-3'-monophosphorous acid, the third valency being saturated by chlorine or a tertiary amino group, for example a morpholino radical. The yields of the individual steps in the synthesis can be determined in each case following the detritylation reaction (b) by spectrophotometry, measuring the absorption of the dimethoxytrityl cation at a wavelength of 496 nm.

After the synthesis of the oligonucleotide is complete, the methyl phosphate protective groups of the oligomer are eliminated using p-thiocresol and triethylamine.

Then the oligonucleotide is removed from the solid carrier by treatment with ammonia for 3 hours. Treatment of the oligomers with concentrated ammonia for 2 to 3 days quantitatively eliminates the amino-protective groups of the bases. The crude product thus obtained is purified by high-pressure liquid chromatography (HPLC) or by polyacrylamide gel electrophoresis.

The other structural units Ib-IIII of the gene are also synthesized entirely correspondingly, their nucleotide sequence being derived from DNA sequence II.

2. Enzymatic Linkage of the Single-Stranded Oligonucleotides to Give the Gene Fragments IFN-I, IFN-II and IFN-III For the phosphorylation of the oligonucleotides at the 5' terminal end, 1 nmol of each of the oligonucleotides Ia and Ib with 5 nmol of adenosine triphosphate were treated with four units of T4-polynucleotide kinase in 20 μl of 50 mM tris HCl buffer (pH 7.6), 10 mM magnesium chloride and 10 mM dithiothreitol (DTT) at 37° C. for 30 minutes (C. C. Richardson, Progress in Nucl. Acids Res. 2 (1972) 825). The enzyme is deactivated by heating at 95° C. for 5 minutes. Then the oligonucleotides Ia and Ib are hybridized with respect to one another by heating them in aqueous solution at 95° C. for 2 minutes and then slowly cooling to 5° C.

The oligonucleotides Ic and Id, Ie and If or Ig and Ih, and Ii and Ij are phosphorylated and hybridized in pairs analogously. Phosphorylation and pairwise hybridization of oligonucleotides IIa with IIb and so on up to IIk with IIl are carried out for subfragment IFN-II, and of oligomers IIIa with IIIb and so on up to IIIk with IIIl for subfragment IFN-III.

The five pairs of oligonucleotides for gene fragment IFN-I and the six pairs of oligonucleotides for gene fragments IFN-II and IFN-III, which are thus obtained, are ligated in each case as follows:

The double-stranded nucleotides are combined and each ligated in 40 μl of 50 mM tris HCl buffer, 20 mM magnesium chloride and 10 mM DTT using 100 units of T4-DNA ligase at 15° C. over the course of 16 hours.

The purification of gene fragments IFN-I to IFN-III is carried out by gel electrophoresis on a 10% polyacrylamide gel (no addition of urea, 20×40 cm, 1 mm thick), the marker substance which was used being φX 174 DNA (supplied by BRL), cut with Hinf I, or pBR 322, cut with Hae III.

3. Preparation of Hybrid Plasmids Which Contain the Gene Fragments IFN-I, IFN-II and IFN-III (a) Incorporation of Gene Fragment IFN-I into pBR 322

The commercially available plasmid pBR 322 is opened in known manner using the restriction endonucleases Eco RI and Bam HI in accordance with the data of the manufacturers. The digestion mixture is fractionated by electrophoresis on a 5% polyacrylamide gel in known manner, and the fragments are visualized by staining with ethidium bromide or by radioactive labeling ("nick translation"method of Maniatis, loc. cit.). The plasmid band is then cut out of the acrylamide gel and separated from the polyacrylamide by electrophoresis. The fractionation of the digestion mixture can also be carried out on 2 % low-melting agarose gels (as described in Example 6(a)).

Figure 1:
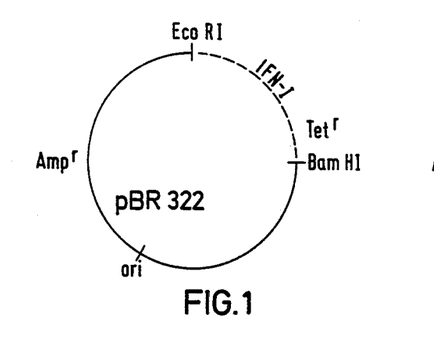

1 μg of plasmid is then ligated with 10 ng of gene fragment IFN-I at 16° C. overnight. The hybrid plasmid shown in FIG. 1 is obtained.

(b) Incorporation of Gene Fragment IFN-II into pUC 8

Figure 2:
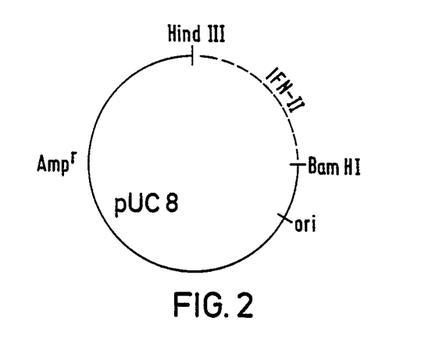

In analogy to (a), the commercially available plasmid pUC 8 is cut open with Bam HI and Hind III, and ligated with gene fragment IFN-II. The hybrid plasmid shown in FIG. 2 is obtained.

(c) Incorporation of gene fragment IFN-III into pUC 8

Figure 3:
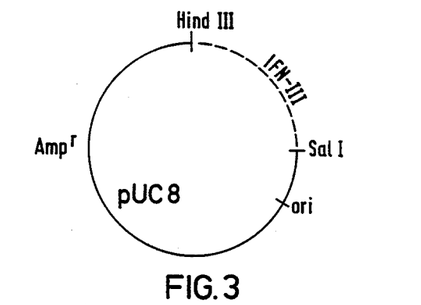

In analogy to (a), the plasmid pUC 8 is cut open with Hind III and Sal I, and ligated with gene fragment IFN-III. The hybrid plasmid shown in FIG. 3 is obtained.

4. Synthesis of the complete gene (a) Transformation and Amplification

The hybrid plasmids thus obtained are transformed into E. coli. For this purpose, the strain E. coli K 12 is made competent by treatment with a 70 mM calcium chloride solution, and the suspension of the hybrid plasmid in 10 mM tris HCl buffer (pH 7.5), which is 70 mM in calcium chloride, is added. The transformed strains are selected as usual, utilizing the resistance or sensitivity to antibiotics conferred by the plasmid, and the hybrid vectors are amplified. After killing the cells, the hybrid plasmids are isolated, cut open with the restriction enzymes originally used, and the gene fragments IFN-I, IFN-II and IFN-III are isolated by gel electrophoresis.

(b) Linkage of the Gene Fragments

The subfragments IFN-I, IFN-II and IFN-III which are obtained by amplification are enzymatically linked as described in Example 2, and the synthetic gene which is thus obtained and has the DNA sequence I is introduced into the cloning vector pUC 8. A hybrid plasma as shown in FIG. 4 is obtained.

5. Synthesis of Hybrid Plasmids Which Contain the DNA Sequences IA, IB and IC.

(a) Hybrid Plasmid Containing the Insert IB

Figure 4:
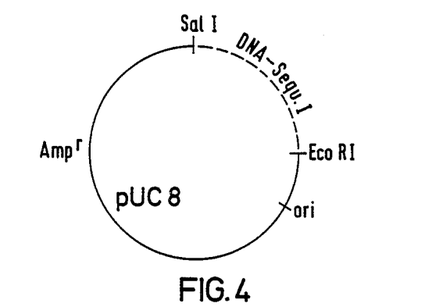

The hybrid plasmid as shown in FIG. 4, which contains DNA sequence I, is cut by known methods using the restriction enzymes Eco RI and Sal I, the small Eco

Figure 5:
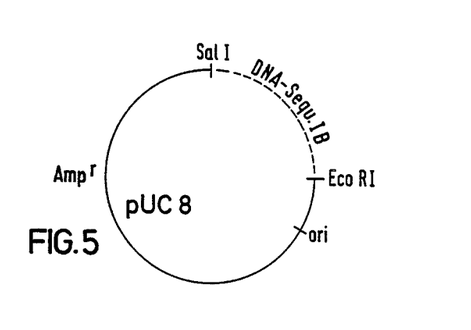

RI and Sal I fragment is removed by polyacrylamide gel electrophoresis, and is then cut using the enzyme Ava II. Using the following adaptor and after ligation with the previously produced large DNA fragment, a hybrid plasmid which contains an insert of DNA sequence IB is obtained (FIG. 5).

(b) Hybrid Plasmid Containing the Insert IA

Figure 6:
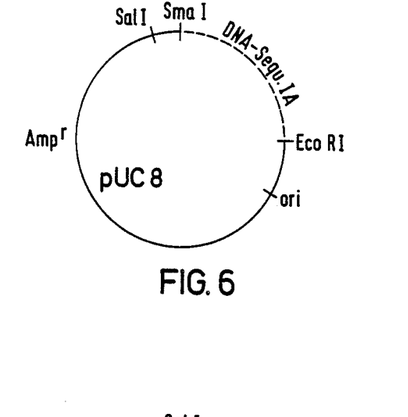

DNA sequence I is cut using the restriction enzyme Pst I in accordance with the data of the manufacturer, and the Eco RI-Pst I fragment is isolated. In addition, the commercially available plasmid pUC 8 is opened using the restriction enzymes Eco RI and Sma I, and the previously isolated fragment is inserted, using the following adaptor whereupon a hybrid plasmid as shown in FIG. 6 is obtained.

(c) Hybrid Plasmid Containing the Insert IC

Figure 7:
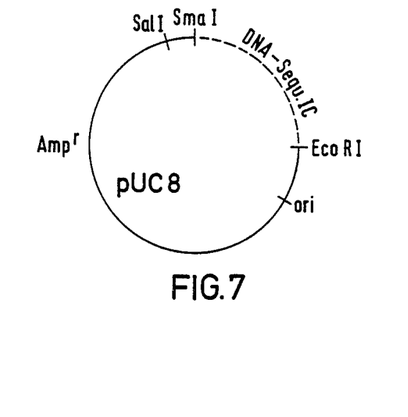

The hybrid plasmid resulting from Example 5a is subjected to digestion with Eco RI and Pst I. The isolated (Eco RI - Pst I) fragment is ligated in analogy to 5b) to give a new hybrid plasmid which now contains an insert of DNA sequence IC (FIG. 7).

6. Construction of Hybrid Plasmids for the Expression of DNA Sequences IA, IB and IC (a) Incorporation into pKK 177.3

The expression plasmid pKK 177.3 (plasmid ptac 11, Amman et al., Gene 25 (1983) 167, into which has been synthetically incorporated, in the Eco RI recognition site, a sequence which contains a Sal I restriction site) is opened using the restriction enzymes Eco RI and Sal I. The insert IB is cut out of the plasmid corresponding to FIG. 5 using the restriction enzymes Eco RI and Sal I. The (slightly longer) inserts IA* and IC* are also isolated in the same manner, since a Sal I restriction site is located in plasmid pUC 8 only a few nucleotides downstream of the actual end of the two gene fragments, characterized by the restriction site of the restriction enzyme Sma I (FIGS. 6 and 7).

Fragments IA*, IB and IC* are applied to 2% low-melting agarose, separated from the plasmid DNA, and the inserts are recovered by dissolving the gel at elevated temperature (in accordance with the statements of the manufacturers). A hybrid plasmid in which, in each case, an expression or regulation region is included upstream of the inserts is obtained by ligation of the plasmid pKK 177.3, which has been cut open, with the fragments IA* and IB or IC*. After addition of a suitable inducer, such as isopropyl-β-thiogalactopyranoside (IPTG), a mRNA is formed, and this leads to the expression of the methionylpolypeptides corresponding to DNA sequences IA and IB or IC.

(b) Incorporation into pMX 2

Figure 8:
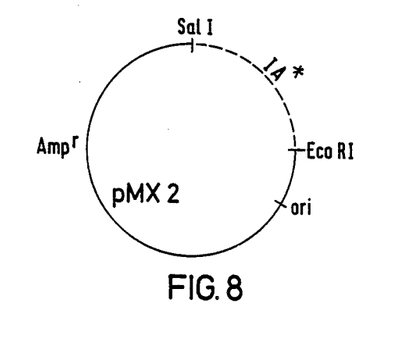
Figure 9:
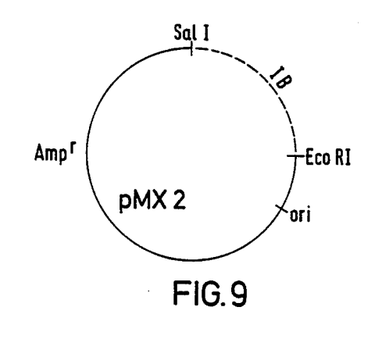
Figure 10:
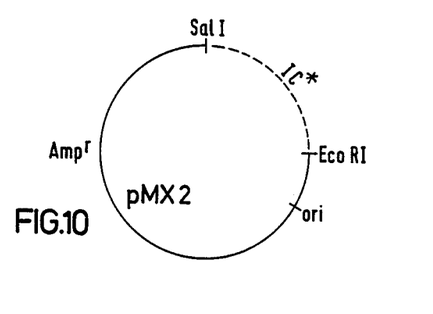

The expression plasmid pMX 2 comprises a pUC 8 plasmid which has been shortened by 21 nucleotides and is prepared in the following manner:

pUC 8 is opened using the restriction endonuclease Eco RI and then treated with the exonuclease Bal 31 under conditions which permit elimination of about 20 nucleotides on both sides of the Eco RI restriction site (Maniatis loc. cit.). Then, any protruding ends of the plasmid thus treated are filled using Klenow DNA polymerase, the plasmid is then cut using the restriction endonuclease Hind III, and the plasmid is purified on 1% low-melting agarose gels in accordance with the statements of the manufacturers. The polylinker, which was originally present in pUC 8 and was limited by the Eco RI and Hind III restriction enzyme cutting sites and had been destroyed by the manipulations described above, is reinserted in the plasmid. For this purpose, pUC 8 is opened using the restriction enzyme Eco RI, and the protruding ends are filled using Klenow DNA polymerase and $^{32}$P-labeled nucleoside triphosphates. The polylinker is then cut out of the plasmid using the restriction enzyme Hind III, and is removed from the plasmid by electrophoresis on 10% acrylamide gels. After identification of the polylinker band using autoradiography, residues of acrylamide are removed from the polylinker by electroelution, and it is ligated into the shortened pUC 8 plasmid. The plasmid pMX 2 thus constructed is then opened using the restriction enzymes Eco RI and Sal I, and is ligated with the γ-interferon gene fragments IA* and IB or IC*, whose ends have Eco RI and Sal I recognition sequences, to give the expression plasmid pMX 2 (FIGS. 8 to 10). Clones which exhibit a high titer of interferon are then identified by determination of the biological activity.

7. Transformation of the Hybrid Plasmids

Competent E. coli cells are transformed with 0.1 to 1 μg of the hybrid plasmids which contain the sequences IA or IB or IC, and are plated onto agar plates containing ampicillin. It is then possible to identify clones which contain the correctly integrated γ-interferon gene sequences in the appropriate plasmids by DNA rapid work-up (Maniatis loc. cit.).

8. Expression of the Polypeptides Exhibiting γ-Interferon Activity

After transformation of the abovementioned hybrid plasmids into E. coli, the polypeptides expressed are those which, in addition to the appropriate γ-interferon aminoacid sequences, carry an additional methionyl group on the amino terminal end, namely in the construction IA, Met-(IFN-γ, aminoacids 1-127), in the construction IB, Met-(IFN-γ, aminoacids 5-146), and in the construction IC, Met-(IFN-γ, aminoacids 5-127).

9. Working Up and Purification

The strains of bacteria which have been cultured to the desired optical density are incubated with a suitable inducer, for example IPTG, for a sufficient time, for example 2 hours. Then the cells are killed using 0.1 % cresol and 0.1 mM benzylsulfonyl fluoride. After centrifugation or filtration, the biomass is taken up in a buffer solution (50 mM tris, 50 mM EDTA, pH 7.5) and disrupted mechanically, for example using a French press or ®DYNO mill (supplied by Willy Bachofer, Basel), whereupon the insoluble constituents are removed by centrifugation. The proteins containing γ-interferon activity are purified from the supernatant by customary processes. Ion exchange, adsorption and gel filtration columns or affinity chromatography on antibody columns are suitable. The enrichment and purity of the products are checked by analysis using sodium dodecyl sulfate/acrylamide gels or HPLC.

Indicator cell lines, such as, for example, Vero cells, are used in known manner for the biological characterization of the products for γ-interferon activity, and are incubated with serial dilutions of bacterial extracts containing interferon. Then, a check is carried out, by infection with a virus such as VSV (vesicular stomatitis virus), of the dilution step up to which the pretreatment of the Vero cells with the bacterial extract was able to achieve an antiviral status. Evaluation can be by microscopy or by determination of the uptake of neutral red.

Moreover, the γ-interferon activity can be determined using a commercially available radioimmunoassay (Celltech Ltd.) which is based on a monoclonal antibody to γ-interferon.

10. Modifications of the DNA Sequence (a) To prepare a γ-interferon analog in which glutamic acid replaces serine in position 102, the following nucleotide is synthesized in accordance with Examples 1 and 2:

```
                              Glu
5' AG CTT ACT AAC TAC GAA GTT ACT GAT TT
3'       A TGA TTG ATG CTT CAA TGA CTA AA
   Hind III                        Aha III
```

The gene fragment IFN-III is digested with the restriction enzyme Aha III, and the larger fragment is removed and ligated with the abovementioned nucleotide. Incorporation in pUC 8 is carried out in accordance with Example 3(c). After transformation and amplification in accordance with Example 4(a), the modified sequence IFN-III is verified by Maxam-Gilbert sequencing. Ligation of this modified subfragment with the gene fragments IFN-I and IFN-II in accordance with Example 4, and continuation of the procedure in accordance with Examples 5 to 9, provides a modified γ-IFN in which glutamic acid is incorporated in place of serine at position 102. This product exhibits antiviral activity.

(b) γ-Interferon analog having the aminoacid sequence 1 to 136 followed by cysteine.

The nucleotide

```
5'              GCT AAA ACT GGT AAA CGT AAA
3' A      CGT CGA TTT TGA CCA TTT GCA TTT
  Pst I

Cys
5' CGT TCC CAG TGC TAA TAG
3' GCA AGG GTC ACG ATT ATC AGC T
                                   Sal I
``` is synthesized in accordance with Examples 1 and 2. The fragment IFN-III is cut using the restriction enzyme Pst I and the larger fragment is separated off. This is ligated with the abovementioned nucleotide, and the procedure is continued as indicated above. A modified γ-interferon which contains aminoacids 1 to 136 and cysteine at the carboxyl terminal end is obtained. This γ-interferon analog is internally stabilized and may be more readily manipulated by chromatography in the work-up than the natural γ-interferon.

DNA sequence I here shown with the sequence characteristic for Eco RI and "triplet No. 0" at the amino terminal end and two stop triplets and the sequence characteristic for Sal I at the carboxy terminal end

| Triplet No. | | | | 0 | 1 | 2 | 3 | 4 | 5 |
|---|---|---|---|---|---|---|---|---|---|
| Aminoacid | | | | Met | Cys | Tyr | Cys | Gln | Asp |
| Nucleotide No. | | 1 | | | 10 | | | 20 | |
| Cod. strand | | 5' AA | TTC | ATG | TGC | TAC | TGC | CAG | GAC |
| Non-cod. strand | | 3' | G | TAC | ACG | ATG | ACG | GTC | CTG |
| 6 | 7 | 8 | 9 | 10 | 11 | 12 | 13 | 14 | 15 |
| Pro | Try | Val | Lys | Glu | Ala | Glu | Asn | Leu | Lys |
| | | 30 | | | 40 | | | 50 | |
| CCG | TAC | GTT | AAA | GAA | GCT | GAA | AAC | CTG | AAA |
| GGC | ATG | CAA | TTT | CTT | CGA | CTT | TTG | GAC | TTT |
| 16 | 17 | 18 | 19 | 20 | 21 | 22 | 23 | 24 | 25 |
| Lys | Tyr | Phe | Asn | Ala | Gly | His | Ser | Asp | Val |
| | | 60 | | | 70 | | | 80 | |
| AAA | TAC | TTC | AAC | GCT | GGT | CAT | TCT | GAC | GTT |
| TTT | ATG | AAG | TTG | CGA | CCA | GTA | AGA | CTG | CAA |
| 26 | 27 | 28 | 29 | 30 | 31 | 32 | 33 | 34 | 35 |
| Ala | Asp | Asn | Gly | Thr | Leu | Phe | Leu | Gly | Ile |
| | | 90 | | | 100 | | | 110 | |
| GCT | GAC | AAT | GGT | ACT | CTG | TTC | CTG | GGG | ATC |
| CGA | CTG | TTA | CCA | TGA | GAC | AAG | GAC | CCC | TAG |
| 36 | 37 | 38 | 39 | 40 | 41 | 42 | 43 | 44 | 45 |
| Leu | Lys | Asn | Trp | Lys | Glu | Glu | Ser | Asp | Arg |
| | | 120 | | | 130 | | | 140 | |
| CTG | AAA | AAC | TGG | AAA | GAA | GAA | TCT | GAC | CGT |
| GAC | TTT | TTG | ACC | TTT | CTT | CTT | AGA | CTG | GCA |
| 46 | 47 | 48 | 49 | 50 | 51 | 52 | 53 | 54 | 55 |
| Lys | Ile | Met | Gln | Ser | Gln | Ile | Val | Ser | Phe |
| | | 150 | | | 160 | | | 170 | |
| AAA | ATC | ATG | CAA | TCT | CAG | ATC | GTT | TCT | TTC |
| TTT | TAG | TAC | GTT | AGA | GTC | TAG | CAA | AGA | AAG |
| 56 | 57 | 58 | 59 | 60 | 61 | 62 | 63 | 64 | 65 |
| Tyr | Phe | Lys | Leu | Phe | Lys | Asn | Phe | Lys | Asp |
| | | 180 | | | 190 | | | 200 | |
| TAC | TTC | AAA | CTG | TTC | AAA | AAC | TTT | AAA | GAC |
| ATG | AAG | TTT | GAC | AAG | TTT | TTG | AAA | TTT | CTG |

-continued

| 66 | 67 | 68 | 69 | 70 | 71 | 72 | 73 | 74 | 75 |
|---|---|---|---|---|---|---|---|---|---|
| Asp | Gln | Ser | Ile | Gln | Lys | Ser | Val | Glu | Thr |
|  |  | 210 |  |  | 220 |  |  | 230 |  |
| GAC | CAG | TCT | ATC | CAG | AAA | TCT | GTT | GAA | ACT |
| CTG | GTC | AGA | TAG | GTC | TTT | AGA | CAA | CTT | TGA |

| 76 | 77 | 78 | 79 | 80 | 81 | 82 | 83 | 84 | 85 |
|---|---|---|---|---|---|---|---|---|---|
| Ile | Lys | Glu | Asp | Met | Asn | Val | Lys | Phe | Phe |
|  |  | 240 |  |  | 250 |  |  | 260 |  |
| ATC | AAG | GAA | GAC | ATG | AAC | GTT | AAA | TTT | TTC |
| TAG | TTC | CTT | CTG | TAC | TTG | CAA | TTT | AAA | AAG |

| 86 | 87 | 88 | 89 | 90 | 91 | 92 | 93 | 94 | 95 |
|---|---|---|---|---|---|---|---|---|---|
| Asn | Ser | Asn | Lys | Lys | Lys | Arg | Asp | Asp | Phe |
|  |  | 270 |  |  | 280 |  |  | 290 |  |
| AAC | TCT | AAC | AAA | AAA | AAA | CGT | GAC | GAC | TTC |
| TTG | AGA | TTG | TTT | TTT | TTT | GCA | CTG | CTG | AAG |

| 96 | 97 | 98 | 99 | 100 | 101 | 102 | 103 | 104 | 105 |
|---|---|---|---|---|---|---|---|---|---|
| Glu | Lys | Leu | Thr | Asn | Tyr | Ser | Val | Thr | Asp |
|  |  | 300 |  |  | 310 |  |  | 320 |  |
| GAA | AAG | CTT | ACT | AAC | TAC | TCT | GTT | ACT | GAT |
| CTT | TTC | GAA | TGA | TTG | ATG | AGA | CAA | TGA | CTA |

| 106 | 107 | 108 | 109 | 110 | 111 | 112 | 113 | 114 | 115 |
|---|---|---|---|---|---|---|---|---|---|
| Leu | Asn | Val | Gln | Arg | Lys | Ala | Ile | His | Glu |
|  |  | 330 |  |  | 340 |  |  | 350 |  |
| TTA | AAC | GTT | CAA | CGT | AAA | GCT | ATC | CAC | GAG |
| AAT | TTG | CAA | GTT | GCA | TTT | CGA | TAG | GTG | CTC |

| 116 | 117 | 118 | 119 | 120 | 121 | 122 | 123 | 124 | 125 |
|---|---|---|---|---|---|---|---|---|---|
| Leu | Ile | Gln | Val | Met | Ala | Glu | Leu | Ser | Pro |
|  |  | 360 |  |  | 370 |  |  | 380 |  |
| CTC | ATC | CAG | GTT | ATG | GCT | GAA | CTG | TCT | CCT |
| GAG | TAG | GTC | CAA | TAC | CGA | CTT | GAC | AGA | GGA |

| 126 | 127 | 128 | 129 | 130 | 131 | 132 | 133 | 134 | 135 |
|---|---|---|---|---|---|---|---|---|---|
| Ala | Ala | Lys | Thr | Gly | Lys | Arg | Lys | Arg | Ser |
|  |  | 390 |  |  | 400 |  |  | 410 |  |
| GCA | GCT | AAA | ACT | GGT | AAA | CGT | AAA | CGT | TCC |
| CGT | CGA | TTT | TGA | CCA | TTT | GCA | TTT | GCA | AGG |

| 136 | 137 | 138 | 139 | 140 | 141 | 142 | 143 | 144 | 145 |
|---|---|---|---|---|---|---|---|---|---|
| Gln | Met | Leu | Phe | Arg | Gly | Arg | Arg | Ala | Ser |
|  |  | 420 |  |  | 430 |  |  | 440 |  |
| CAG | ATG | CTG | TTC | CGC | GGT | CGT | CGT | GCT | TCT |
| GTC | TAC | GAC | AAG | GCG | CCA | GCA | GCA | CGA | AGA |

| 146 |
|---|
| Gln |
| 450 |
| CAG TAA TAG            3' |
| GTC ATT ATC AGC T      5' |

DNA sequence I A: here shown with the sequence characteristic for Eco RI and "triplet No. 0" at the amino terminal end and two stop triplets and the sequence characteristic for Sma I        at the carboxy terminal end
                    0
                    Met (aminoacids 1-127) Stp Stp
        1     5
5'  AA    TTC ATG (nucleotides 9-389) TAG TAA CCC 3'
        G TAC (complementary           ATC ATT GGG
             nucleotides)

DNA sequence I B: here shown with the sequence characteristic for Eco RI and "triplet No. 0" at the amino terminal end and two stop triplets and the sequence characteristic for Sal I at the carboxy terminal end
                    0
                    Met (aminoacids 5-146) Stp Stp
5'              AA    TTC ATG (nucleotides 21-446)
                                        TAA TAG      3'
            G TAC                       ATT ATC AGC T 5'

DNA sequence I C: here shown with the sequence characteristic for Eco RI and "triplet No. 0" at the amino terminal end and two stop triplets and the sequence characteristic for

Sma I        at the carboxy terminal end
                    0
                    Met (aminoacids 5-127) Stp Stp
5'              AA    TTC ATG (nucleotides 21-389)
                                        TAG TAA CCC 3'
            G TAC                       ATT ATC GGG DNA sequence II IFN-I:

←————————Ia————————→

Met Cys Tyr Cys Gln Asp
5' AA TTC ATG TGC TAC TGC CAG GAC
3'     G    T ACACG ATG ACG GTC CTG
Eco RI ←————————————Ib————————

←————————————Ic————————————→×
|Pro Tyr Val Lys Glu Ala Glu Asn |Leu Lys
|CCG TAC GTT AAA GAA GCT GAA AAC |CTG AAA
|GGC ATG CAA TTT CTT CGA CTT TTG |GAC TTT
————————————Id————————————→×

DNA sequence II IFN-II:

What is claimed:

```
            ———————————>
            Gln Stp Stp
            CAG TAA TAG         3'
            GTC ATT ATC AGC T   5'
            ———————————>
                              Sal I
```

1. Partial sequences of human gamma interferon (IFN-γ) selected from the sequences consisting of aminoacid sequences 5 to 127, 1 to 127 and 5 to 146, of the amino acid sequence:

$Cys^1$—Tyr—Cys—Gln—Asp—Pro—Tyr—Val—Lys—$Glu^{10}$—

Ala—Glu—Asn—Leu—Lys—Lys—Tyr—Phe—Asn—$Ala^{20}$—

Gly—His—Ser—Asp—Val—Ala—Asp—Asn—Gly—$Thr^{30}$—

Leu—Phe—Leu—Gly—Ile—Leu—Lys—Asn—Trp—$Lys^{40}$—

Glu—Glu—Ser—Asp—Arg—Lys—Ile—Met—Gln—$Ser^{50}$—

Gln—Ile—Val—Ser—Phe—Tyr—Phe—Lys—Leu—$Phe^{60}$—

Lys—Asn—Phe—Lys—Asp—Asp—Gln—Ser—Ile—$Gln^{70}$—

Lys—Ser—Val—Glu—Thr—Ile—Lys—Glu—Asp—$Met^{80}$—

Asn—Val—Lys—Phe—Phe—Asn—Ser—Asn—Lys—$Lys^{90}$—

Lys—Arg—Asp—Asp—Phe—Glu—Lys—Leu—Thr—$Asn^{100}$—

Tyr—Ser—Val—Thr—Asp—Leu—Asn—Val—Gln—$Arg^{110}$—

Lys—Ala—Ile—His—Glu—Leu—Ile—Gln—Val—$Met^{120}$—

Ala—Glu—Leu—Ser—Pro—Ala—Ala—Lys—Thr—$Gly^{130}$—

Lys—Arg—Lys—Arg—Ser—Gln—Met—Leu—Phe—$Arg^{140}$—

Gly—Arg—Arg—Ala—Ser—$Gln^{146}$.

2. A medicament containing an amount of the aminoacid sequences as claimed in claim 1 effective for use as an antiviral, antitumoral, antineoplastic or immunomodulating agent.

* * * * *